United States Patent [19]

Perboni et al.

[11] Patent Number: 5,196,528
[45] Date of Patent: Mar. 23, 1993

[54] 4-CYCLOHEXENYL AZETIDINONES AND EPOXY DERIVATIVES THEREOF

[75] Inventors: Alcide Perboni, San Giorgio di Mantova; Claudio Bismara, Oppeano; Giorgio Pentassuglia, Trento, all of Italy

[73] Assignee: Glaxo S.p.A., Verona, Italy

[21] Appl. No.: 729,146

[22] Filed: Jul. 12, 1991

[30] Foreign Application Priority Data

Jul. 13, 1990 [GB] United Kingdom ............... 9015485

[51] Int. Cl.$^5$ ............... C07D 205/08; C07D 405/08; C07D 487/04
[52] U.S. Cl. ............... 540/200; 540/302
[58] Field of Search ............... 540/200

[56] References Cited

FOREIGN PATENT DOCUMENTS 416952 3/1991 European Pat. Off. .

*Primary Examiner*—Mark L. Berch
*Attorney, Agent, or Firm*—Bacon & Thomas

[57] ABSTRACT

Compounds of formula

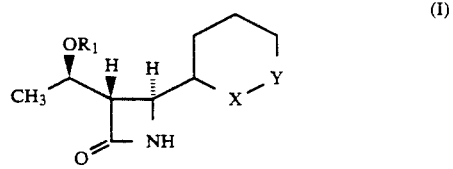

(I)

in which $R_1$ is hydrogen or a hydroxyl protecting group and —X—Y— is —CH=CH— or

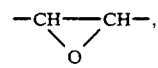

useful as intermediates in the preparation of antibacterially active compounds.

9 Claims, No Drawings

4-CYCLOHEXENYL AZETIDINONES AND EPOXY DERIVATIVES THEREOF

This invention relates to novel heterocyclic compounds useful in the preparation of compounds having antibacterial activity, and to processes for their preparation.

Thus the present invention provides compounds of the general formula (I)

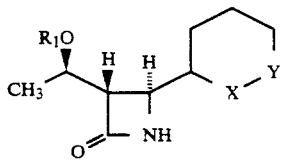
(I)

in which $R_1$ represents a hydrogen atom or a hydroxyl protecting group and —X—Y— represents the group —CH=CH— or the epoxide group (A).

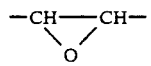
(A)

Suitable hydroxyl protecting groups $R_1$ include those which may be removed by hydrolysis under buffered conditions or under non-aqueous conditions.

When the group $OR_1$ is a protected hydroxyl group this is conveniently an ether or an acyloxy group. Examples of particularly suitable ethers include those in which $R_1$ is a hydrocarbylsilyl group such as trialkylsilyl, e.g. tri($C_{1-6}$alkyl)silyl such as trimethylsilyl or more especially t-butyldimethylsilyl. When the group $OR_1$ represents an acyloxy group then examples of suitable groups $R_1$ includes alkanoyl e.g. acetyl or pivaloyl; alkenoyl e.g. allylcarbonyl; aroyl e.g. p-nitrobenzoyl; alkoxycarbonyl e.g. t-butoxycarbonyl; haloalkoxycarbonyl e.g. 2,2,2-trichloroethoxycarbonyl, or 1,1,1-trichloro-2-methyl-2-propoxycarbonyl; aralkyloxycarbonyl e.g. benzyloxycarbonyl or p-nitrobenzyloxycarbonyl; or alkenyloxycarbonyl e.g. allyloxycarbonyl.

In formula I the wedge shaped bond ◂ indicates that the bond is above the plane of the paper. The broken bond ⦀ indicates that the bond is below the plane of the paper.

In addition to the fixed stereochemical arrangement as defined in formula (I) the molecule contains at least one further centre of asymmetry, and when X—Y is the epoxide group (A) there are also two additional centres of asymmetry. All stereoisomers including mixtures thereof arising from these additional asymmetric centres are within the scope of the compounds of formula (1). The specific stereoisomers of formula (I) may be represented by formulae (1a) to (1f).

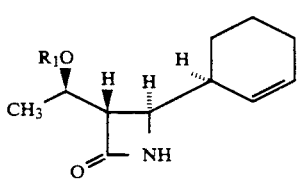
(1a)

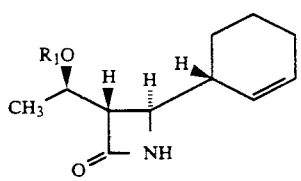
(1b)

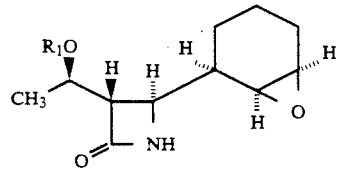
(1c)

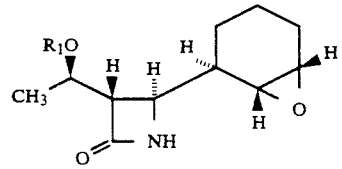
(1d)

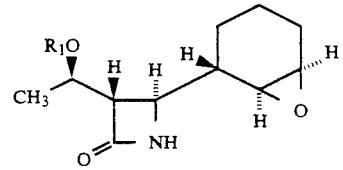
(1e)

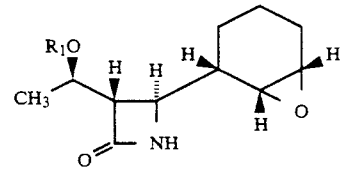
(1f)

Preferred compounds of the invention include those of formula (1a); of the corresponding compounds (1) in which X—Y represents the epoxide group (A) the compounds of formula (1c) are particularly preferred.

Particularly preferred compounds of formula (I) are those wherein $R_1$ represent a hydroxyl protecting group.

The compound of formula (I) in which $R_1$ represents a hydroxyl protecting group and X—Y represent the epoxide group (A) may be prepared by epoxidation of the corresponding compound of formula (I) in which X—Y represents the group —CH=CH—. The epoxidation may conveniently be carried out by treating the cycloalkene of formula (I) with a peracid. Suitable peracids include optionally substituted perbenzoic acids such as perbenzoic acid or meta chloroperbenzoic acid, peralkanoic acids such as peracetic acid and trifluoroperacetic acid and salts of monoperoxyphthalic acid such as the magnesium salt thereof. The reaction may be carried out in a solvent such as a halohydrocarbon e.g. dichloromethane and conveniently at a temperature within the range −30° to +30° C. For the reaction using a salt of monoperoxyphthalic acid this is conveniently carried out in the presence of water and a water immiscible solvent, for example a halohydrocarbon such as dichloromethane. For this epoxidation reaction it is desirable to use a protecting group $R_1$ which does not contain an alkenyl grouping.

The compounds of formula (I) in which X—Y is the group —CH=CH— may be prepared by treating the corresponding tosylhydrazone (II)

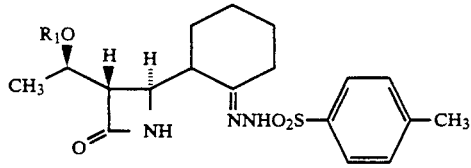

in which $R_1$ is a hydroxyl protecting group with a base such as an alkyl lithium e.g. methyl or butyl lithium or lithium diisopropylamide. The reaction is conveniently carried out in an aprotic solvent such as an ether e.g. tetrahydrofuran and at a temperature between −50° C. and 0° C.

The tosylhydrazone (II) may be prepared by treating the cyclohexanone derivative (III)

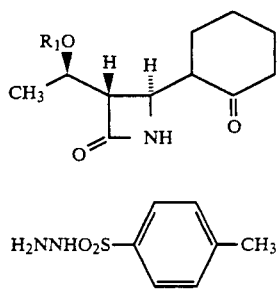

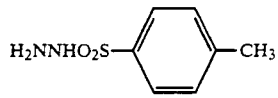

in which $R_1$ is a hydroxyl protecting group with tosyl-hydrazide (IV) in a suitable solvent such as ethyl acetate, an alkanol e.g. methanol or an ether e.g. tetrahydrofuran, in the presence of an acid catalyst e.g. acetic acid.

The cyclohexanone derivative (III) may be prepared by treating the azetidinone (V)

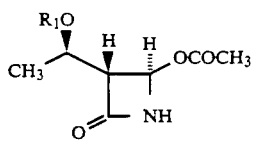

in which $R_1$ is a hydroxyl protecting group with 1-trimethylsilyloxycyclohexene in the presence of trimethylsilyl trifluoromethanesulphonate. This reaction is conveniently carried out in a solvent such as dichloromethane.

In this reaction the cyclohexanone derivative (III) is generally obtained as a mixture of two isomers (IIIa) and (IIIb) and if required these two compounds may be separated by conventional procedures such as column chromatography.

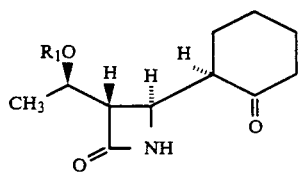

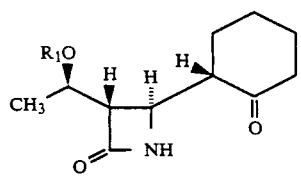

The azetidinones of formula (V) are either known compounds or may be prepared by analogous methods to those described for the known compounds.

Alternatively compounds of formula (Ia) in which $R_1$ represents a hydroxyl protecting group may be prepared from the azetidinone (V) by reaction with a 3-halo-cyclohexene such as 3-bromo- cyclohexene in the presence of a metal such as tin or zinc and in a suitable solvent such as an ether e.g. tetrahydrofuran or diethyl ether or a hydrocarbon such as benzene or toluene.

The individual isomers of formula (I) as represented by formulae (1a) to (1f) may be prepared by the general processes described above using the appropriate stereoisomer of the starting material. Thus if the epoxidation reaction is carried out using compound of formula (1a), the product of the reaction will be a compound of formula (1c) or (1d) or a mixture thereof depending on the oxidising agent used and the reaction conditions.

The use of a corresponding compound (Ib) as starting material will give a compound (1e) or (1f) or a mixture thereof.

The compounds (1c) and (1d), and/or (1e) and (1f) may be separated from each other by conventional procedures such as column chromatography.

The stereoisomers of formula (1a) or (1b) may be prepared by the procedures described above starting with the appropriate cyclohexanone (IIIa) or (IIIb).

Compounds of formula (I) in which $R_1$ represents a hydrogen atom may be prepared from a compound in which $R_1$ represents a hydroxyl protecting group by the use of conventional procedures for the removal of such groups.

Compounds of formula (I) in which $R_1$ represents a hydroxyl protecting group, including those containing an alkenyl moiety, may be prepared from the compound of formula (I) in which $R_1$ represents a hydrogen atom using conventional procedures for preparing such protected hydroxyl functions.

The compounds of formula (I) are useful intermediates for the preparation of compounds having useful antibacterial activity. Thus the compounds of formula (I) may be used to prepare the antibacterial compounds described in European Patent Application Publication No. 0416953A. For example the compounds (1) may be used to prepare compounds of formula (VI)

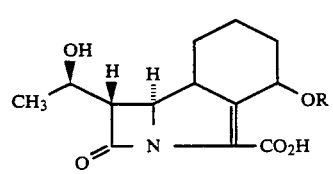

in which R is a $C_{1-5}$ alkyl group, for example methyl, and salts thereof. These compounds exhibit a broad spectrum of antibacterial activity against a wide range of pathogenic microorganisms and have a very high resistance to all β-lactamases.

The compounds of formula (VI) may be prepared from compounds of formula (I) in which X—Y is the group (A) using the following reaction sequence.

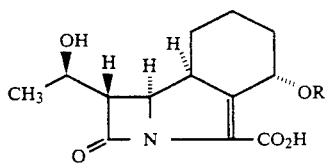

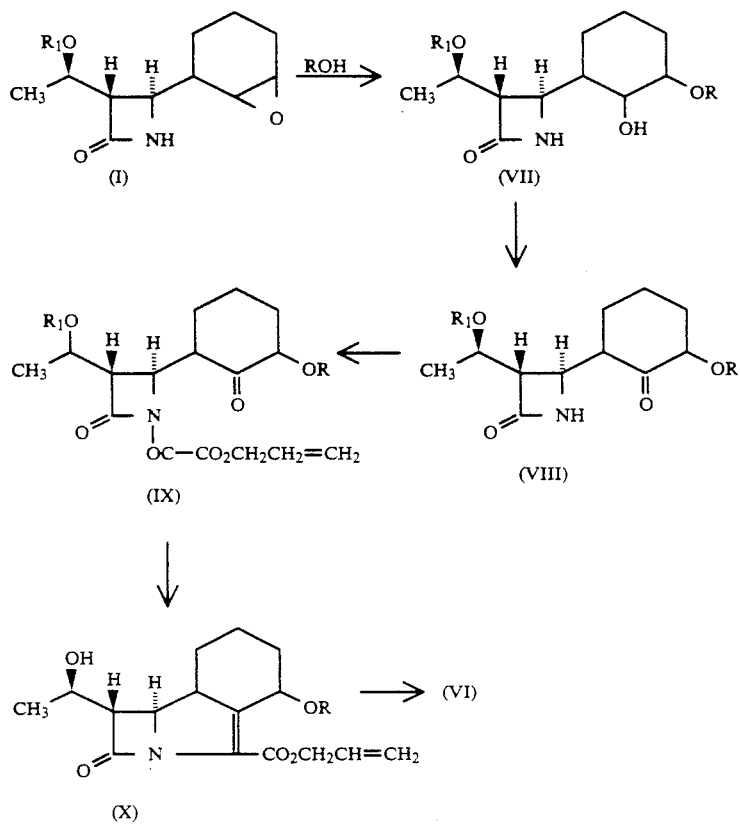

Reaction of the epoxide (I) with the alcohol ROH in the presence of an acid catalyst such as p-toluenesulphonic acid gives the hydroxyether (VII). Treatment of compounds (VII) with a suitable oxidising agent such as pyridinium chlorochromate yields the required keto ether (VIII). Reaction of the keto ether (VIII) with allyloxalylchloride in the presence of triethylamine gives the oxalimido intermediate (IX). The reaction of compound (IX) with an organic phosphite such as triethylphosphite yields the tricyclic derivative (X). This compound which is a protected derivative of compound (VI) may be converted into compound (VI) or a salt thereof by first removal of the hydroxyl protecting group R₁ and then hydrolysis of the allyl ester. The removal of the hydroxyl protecting group R₁ may be carried out using standard conditions known for the removal of such groups. The allyl ester may be hydrolysed for example by treatment with an allyl acceptor such as 2-ethyl hexanoic acid, or a sodium or potassium salt thereof, in the presence of tetrakis (triphenylphosphine) palladium and triphenylphosphine.

In the above reaction sequence the use of a specific stereoisomer of formula (I) as starting material will give a specific isomer of the compound of formula (VI). Thus the epoxide of formula (Ic) will give a compound of formula (VIa).

The compounds of formula (VIa) are particularly useful antibacterial agents and thus the compound of formula (Ic) represents a particularly preferred feature of the invention.

In order that the invention may be more fully understood the following examples are given by way of illustration only.

INTERMEDIATE 1

(3S,4R)-3-[(R)-1-(t-Butyldimethylsilyloxy)ethyl]-4-[(R)-2'-(1,-oxo-cyclohexyl)]azetidin-2-one and (3S,4R)-3-[(R)-1-(t-Butyldimethylsilyloxy)ethyl]-4-[(S)-2'-(1'-oxocyclohexyl)]azetidin-2-one 1-Trimethylsilyloxycyclohexene (11 g) was dissolved in methylene chloride (400 ml) under nitrogen. (3R,4R)-4-Acetoxy-3((R)-(t-butyldimethylsilyloxy)ethyl)-2-azetidinone (9.28 g) was added to the solution, the mixture stirred at 230° C. and trimethylsilyl trifluoromethanesulphonate (0.66 g) was added. The mixture was stirred under nitrogen for 2 hr and then poured into an ice cold 1% solution of sodium hydrogen carbonate (300 ml). The organic layer was separated, washed with water (300 ml) and brine (300 ml). Evaporation of the solvent under reduced pressure gave the title compounds as an oily residue.

INTERMEDIATE 2

(3S,4R)-3-[(R)-1-(t-butyldimethylsilyloxy)ethyl]-4-[[(R)-1'-(4-methylphenylsulphon)hydrazono]-cyclohex-2'-yl]-azetidin-2-one(2a) and (3S,4R)-3-[(R)-1-(t-butyldimethylsilyloxy)ethyl]-4-[[(S)-1'-(4-methylphenylsulphon)hydrazono]-cyclohex-2'-yl]-azetidin-2-one(2b)

To a solution of intermediate 1 (12.1 g) in glacial acetic acid (120 ml) tosylhydazide (6.9 g) was added at room temperature. The reaction was stirred for 3 hr, diluted with dichloromethane (250 ml), washed with brine (2×250 ml), then with a 5% solution of sodium hydrogen carbonate until pH 7, and with brine again (2×150 ml). The organic layer was dried and the solvent evaporated under reduced pressure. The obtained foam was stirred with diethyl ether (60 ml) for 2 hr at room temperature filtered and dried to give the title compound 2b as a white powder, (6 g; m.p. 187 -189° C.; t.l.c. diethyl ether Rf=0.13). IR (CDCl$_3$) V$_{max}$ (CM$^1$) 3416(N-H), 3304(NNHSO$_2$), 1753 (lactam), 15599(C=N; C=C) H$^1$-NMR (CDCl$_3$): 7.80 (d) 7.38 (bm), 7.34(d), 5.65 (bs), 4.15 (m) 3.58 (dd) 2.63(m), 2.62(m), 2.44(s), 2.3(m), 2.08(m), 1.92(m), 1.78(d), 1.4(m), 1.20(m), 1.185(d), 0.9(s), 0.077(s), 0.067(s). The organic layer, which contained the title compound 2a in the presence of a small amount of the title compound 2b (by t.l.c.), was concentrated and the residue was purified by flash chromatography (eluant diethyl ether/petroleum ether 7:3) to give the title compound 2a as a white powder (7.6 g; m.p. 95°-96° C.; t.l.c. diethyl ether Rf-0.37)

IR (CDCl$_3$)V$_{max}$ (cm$^1$) 3410(N-H), 3306(NNHSO$_2$), 1755(lactam), 1599 (C-N; C=C) H$^1$-NMR (CDCl$_3$): 7.81(d), 7.40(m), 7.33(d), 5.60(bs) 4.09(m) 4.00(m), 2.81(dd), 2.52(m), 2.44(s), 2.3(m), 2.0-1.8(m), 1.6-1.4(m), 1.04(d) 0.87(s) 0.06(s), 0.03(s).

EXAMPLE 1

(3S,4R)-3-[(R)-1-(t-butyldimethylsilyloxy)ethyl]-4-[(S)-3'-cyclohex-1-enyl]-azetidin-2-one A solution of the intermediate 2a (1.12 g) in anhydrous tetrahydrofuran (20 ml) was slowly added, at −40° C., to a stirred solution of lithium diisopropylamide (prepared from anhydrous diisopropylamine (1.35 ml) and a 1.6M solution of n-butyllithium in hexane (5.7 ml)). The reaction was slowly warmed to −20°/0° C. and maintained at −20°/0° C. for 1 h. The reaction mixture was added to a precooled 5% solution of hydrochloric acid (20 ml) and extracted with ethyl acetate (2×40 ml). The organic layer was washed with a 5% solution of sodium hydrogen carbonate (20 ml) and brine (20 ml), then dried over anhydrous sodium sulfate and evaporated. The crude product was purified by flash chromatography (eluant diethyl ether/petroleum ether 1/1) to give the title compound as a white powder (0.45 g, m.p. 104°-106° C.; t.l.c. diethyl ether Rf=0.73) IR (CDCl$_3$) V$_{max}$ (CM$^1$) 3416(N-H), 1753 (lactam), 1603(C=C) H$^1$-NMR (CDCl$_3$): 5.82(bs),. 5.81(m), 5.60(dd), 4.14(m), 3.46(dd), 2.85(m), 2.24(m), 2.00(m), 1.85-1.70(m), 1.54(m), 1.27(m) 1.23(d), 0.86(s), 0.064(s), 0.054(s).

EXAMPLE 2

(3S,4R)-3-[(R)-1-(t-butyldimethylsilyloxy)ethyl]-4-[(1'R,2'S,3'R)-1',2'-epoxycyclohex-3,-yl]-azetidin-2-one (2a) and (3S,4R)-3-[(R)-1-(t-butyldimethylsilyloxy)ethyl]-4-[(1'S,2'S,3'R)-1', 2'-epoxycyclohex-3-yl]-azetidin-2-one (2b)

A solution of metachloroperbenzoic acid (3.76 g; assay 55%) in dichloromethane (50 ml) was added dropwise, at 0° C. to a solution of example 1 (3.1 g) in dichloromethane (50 ml). The solution was wad to room temperature and stirred for 3 hr. The reaction mixture was added to a 10% solution of sodium sulphite (50 ml), washed with a 5% solution of sodium hydrogen carbonate (2×50 ml) and brine (50 ml). The solution was dried over anhydrous sodium sulphate and the solvent was evaporated. The crude product was purified by flash chromatography (eluant ethyl acetate/cyclohexane 3/7) to obtain the title compound 2a as a white powder (1.53 g; m.p. 134°-136° C.; t.l.c. diethyl ether Rf=0.3)IR (CDCl$_3$) V$_{max}$ 3413(N-H), 1757 (lactam); $^1$H-NMR (CDCl$_3$): 5.85(bm), 4.22(m), 3.77(dd), 3.16(t), 3.12(m), 3.01(m), 2.00-1.7(m), 1.55(m), 1.4(m), 1.24(d), 1.22(m), 0.87(s), 0.067(s) and title compound 2b as a white powder (0.56 g; m.p. 96°-98°, t.l.c. diethyl ether Rf=0.4) IR (CDCl$_3$)V$_{max}$(cm$^{-1}$)3414 (N-H), 1757(lactam).

EXAMPLE 3

(3S,4R)-3-[(R)-1-(t-Butyldimethylsilyloxy)ethyl]-4-((S)-3'-cyclohex-1,-enyl]azetidin-2-one and
(3S,4R)-3-[(R)-1-(t-butyldimethylsilyloxy)ethyl]-4-[(R)-3'-cyclohex-1,-enyl]azetidin-2-one .

To a stirred suspension of Zinc (6.8 g) (activated with Iodine) in dry tetrahydrofuran (50 ml), a solution of (3R,4R)-4-acetoxy-3-((R)-(t-butyldimethylsilyloxy)ethyl)-2-azetidinone (10 g) and 3-bromo-cyclohexene (14 g) in dry tetrahydrofuran (100 ml) was added dropwise over 6 hrs, at 0° C. under nitrogen. The reaction mixture was allowed to stand at 6° C. for 15 min, then poured into a two-phase mixture of diethylether (300 ml) and cold saturated aq. ammonium chloride (250 ml). The organic layer was separated and washed with saturated aq.ammonium chloride (250 ml), 2% aq. sodium hydrogen carbonate (250 ml), brine (250 ml) and dried over anhydrous sodium sulphate. The solvent was removed in vacuo to afford the title compounds (12.47 g; R/S=55/45) as a white solid.

IR(Nujol) v max(cm−1): 1755(C=O).

H$^1$-NMR(CDCl$_3$) δ (ppm): 6.10(s), 6.00(s), 5.88-5.80(m), 5.61(dd), 5.55(dd), 4.18(m), 3.48-3.40(m), 2.85(m), 2.81(m),2.32-2.10(m), 2.01(m), 1.86-1.64(m), 1.62-1.46(m), 1.40-1.20(m), 1.24(d), 1.22(d), 0.88(s), 0.08(s), 0.06(s).

EXAMPLE 4

(3S,4R)-3-[(R)-1-(t-Butyldimethylsilyloxy)ethyl]-4-[(1′R,2′S,3′R)-1′,2′-epoxycyclohex-3′-yl]azetidin-2-one (4a) and (3S,4R)-3-[(R)-1-t-butyldimethylsilyloxy)ethyl]-4-[(1′S,2′S,3′R)-1′,2′-epoxycyclohex-3-yl]azetidin-2-one (4b)

A solution of example 1 (40 g) in a mixture of water (200 ml) and dichloromethane (400 ml) was treated at 30° C. with magnesium monoperoxyphthalate (80 g; assay 80% w/w). The resulting biphasic mixture was stirred at 50° C. for 24 h and treated with 2M aqueous sodium carbonate (28 oml). The aqueous layer was extracted with dichloromethane (12 oml) and the combined dichloromethane extracts were washed with 10% aqueous sodium metabisulphite (200 ml), dried over magnesium sulphate, and evaporated to give a 94/6 mixture of the title compounds 4a and 4b as a white solid (39.3 g)

$^1$H-NMR (CDCl$_3$): concordant with example 2.

EXAMPLE 5

(3S,4R)-3-[(R)-1-(t-Butyldimethylsilyloxy)-ethyl]-4-[(R)-cyclohex-2-enyl]-azetidin-2-one (5a) and (3S,4R)-3-[(R)-1-(t-butyldimethylsilyloxy)-ethyl]-4-[(S)-cyclohex-2-enyl]-azetidin-2-one (5b)

Boron trifluoride etherate (0.5 ml) was added to a solution of tributylcyclohex-2-enyl stannane (14.5 g) and (3S, 4R)-3-[(R)-1-(t-butyldimethylsilyloxy)-ethyl]-4-acetoxy-azetidin-2-one (3.8 g) in dry dichloromethane (200 ml). The solution was stirred overnight, washed with water, brine and then dried over sodium sulphate. The solvent was evaporated and the residual oil was chromatographed on silica, using petroleum/diethylether (7/3) as eluant, to give the title compounds 5a and 5b in a 75/25 ratio, as a white solid.

IR (CDCl$_3$) V$_{max}$ (cm$^{-1}$): 3416 (MH), 1753 (C=O;

H-NMR s (CDCl$_3$): 5.88(ma), 5.78(m), 5.58(m), 5.51(m), 4.16(m), 4.15(m), 3.43(dd), 3.40(dd), 2.81(m), 2.78(m), 2.18(m), 1.98(m), 1.74(m), 1.54(m), 1.30(m), 1.21(d), 1.19(d), 0.84(s), 0.04(s) ppm.

EXAMPLE 6

(3S,4R)-3-[(R)-1-(t-Butyldimethylsilyloxy)-ethyl]-4-[(S)-(2R, 3s-epoxycyclohexyl)]-azetidin-2-one (6a) and (3S,4R)-3-[(R)-1-(t-Butyldimethylsilyloxy)-ethyl]-4-[(R)-(2S, 3R-epoxycyclohexyl)]-azetidin-2-one (6b) and (3S,4R)-3-[(R)-1-(t-Butyldimethylsilyloxy)-ethyl]-4-[(S)-(2S, 3R-epoxycyclohexyl)]-azetidin-2-one (6c) and (3S,4R)-3-[(R)-1-(t-Butyldimethylsilyloxy)-ethyl]-4-[(R)-(2R, 3S-epoxycyclohexyl)]-azetidin-2-one (6d)

Meta chloroperbenzoic acid (1.69 g) was added to an ice cold solution of Example 5 (2.0 g) in dry dichloromethane (50 ml). The mixture was stirred overnight washed with 5% sodium hydrogen carbonate, water and brine. The organic layer was dried over sodium sulphate and the solvent evaporated. The residual oil was chromatographed on silica using diethylether as eluant to obtain a mixture of title compounds 6a and 6b (0.4 g in a 4:1 ratio) and a mixture of title compounds 6b, 6c and 6d (0.2 g in a 2:2:1 ratio).

Title Compounds 6a & 6b

IR (CDCl$_3$) V$_{max}$ (cm$^{-1}$): 3412 (NH), 1757 (C=O; H-NMR s (CDCl$_3$): 6.13(sa), 5.94(sa), 4.19(m), 3.77(dd), 3.67(dd), 3.25(m), 3.18(t), 3.12(t), 3.01(m), 2.83(dd), 1.88(m), 1.45-1.65(m), 1.15-1.44(m), 0.85(s), 0.07(s) ppm.

Title Compounds 6b & 6c & 6d

IR(CDCl$_3$) V$_{max}$ (cm$^{-1}$): 3414 (NH), 1755 (C=O); H-NMR s (CDCl$_3$): 6.28(sa), 6.16(sa), 6.05(sa), 4.09-4.24(m), 3 78(dd), 3.67(dd), 3.58(dd), 3.19(m), 3.15(m), 3.1(m), 3.01(m), 2.82-2.95(m), 2.04-2.16(d), 1.9-2.03(m), 1.54-1.74(m), 1.32-1.48(m), 1.15-1.31(m), 0.9(sa) 0.06(sa) ppm.

We claim:

1. Compounds of the formula (I)

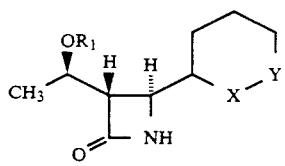

(I)

in which R$_1$ represents a hydrogen atom or a hydroxyl protecting group and —X—Y— represents a group selected from —CH=CH— and

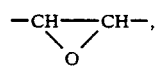

2. Compounds as claimed in claim 1 having the formula (Ia)

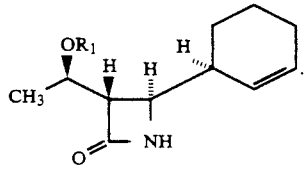

(Ia)

where R$_1$ is as defined in claim 1.

3. Compounds as claimed in claim 1 having the formula (Ic)

(Ic)

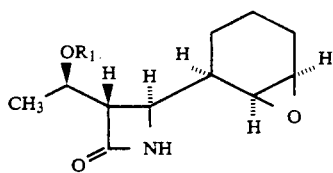

where $R_1$ is as defined in claim 1.

4. Compounds as claimed in claim 1 wherein $R_1$ is a trialkylsilyl group.
5. Compounds as claimed in any of claim 1 wherein $R_1$ is a t-butyldimethylsilyl group.
6. Compounds as claimed in claim 2 wherein $R_1$ is a t-butyldimethylsilyl group.
7. Compounds as claimed in claim 3 wherein $R_1$ is a t-butyldimethylsilyl group.
8. Compounds as claimed in claim 2 wherein $R_1$ is a trialkysilyl group.
9. Compounds as claimed in claim 3 wherein $R_1$ is a trialkysilyl group.

* * * * *